United States Patent [19]

Leturmy et al.

[11] Patent Number: 5,563,338
[45] Date of Patent: Oct. 8, 1996

[54] METHOD AND DEVICE FOR MEASURING WETTABILITY UNDER CONTROLLED ATMOSPHERE

[75] Inventors: Marc Leturmy, Garanciere; Nicolas Potier, Saint Cloud, both of France

[73] Assignee: L'Air Liquide, Societe Anonyme pour l'Etude et l'Exploitation des Procedes Georges Claude, Paris Cedex, France

[21] Appl. No.: 453,891

[22] Filed: May 30, 1995

[30] Foreign Application Priority Data

Jun. 9, 1994 [FR] France .................. 94.07047

[51] Int. Cl.$^6$ .................................................. G01N 13/00
[52] U.S. Cl. .................. 73/64.49; 73/54.22; 73/104; 228/103
[58] Field of Search ................ 73/54.22, 61.42, 73/64.48, 64.52, 64.56, 866, 104, 646.49, 64.56; 228/103, 104, 56.5

[56] References Cited

U.S. PATENT DOCUMENTS

| 2,942,999 | 6/1960 | Roehl et al. ............... 73/866 X |
| 3,060,727 | 10/1962 | Cortiss . | |
| 3,857,290 | 12/1974 | Aitken et al. ............... 73/866 |
| 3,901,088 | 8/1975 | Midgley ...................... 73/866 |
| 4,227,415 | 10/1980 | Spirig ........................ 73/866 |
| 4,694,685 | 9/1987 | Dick ........................... 73/54.22 X |
| 5,121,874 | 6/1992 | Deambrosio et al. ........ 228/219 |

FOREIGN PATENT DOCUMENTS

| 3714012 | 11/1988 | Germany . | |
| 53749 | 4/1977 | Japan ................... 73/64.49 |
| 82039 | 6/1980 | Japan ................... 73/64.49 |
| 97427 | 6/1982 | Japan ................... 73/64.48 |
| 183139 | 7/1990 | Japan ................... 73/64.49 |
| 605153 | 4/1978 | U.S.S.R. ............... 73/54.22 |
| 1255899 | 9/1980 | U.S.S.R. ............... 73/64.48 |

OTHER PUBLICATIONS

C. Morel, "Apparatus for contact angle measurement between molten salts and solids and surface tensions of molten salts at high temperatures", Journal of Scientific Instruments, Sep. 1966, vol. 42, No. 9, pp. 647–648.

A Mehta et al., "Nitrogen-Based Soldering—Tests and Results", Proceedings Technical Program, Jun. 10–13, 1991, pp. 481–490.

*Primary Examiner*—Thomas P. Noland
*Attorney, Agent, or Firm*—Young & Thompson

[57] ABSTRACT

A device making it possible to carry out wettability measurements under a controlled atmosphere, comprising an apparatus (5) for measuring the wettability of at least one surface portion of a sample by a liquid metallic solder, at least partially included in an enclosure (6) which includes a gas injector which comprises at least one set of ducts (10) mounted in series and/or in parallel, at least one portion of which includes gas injection orifices, and is fed by at least one gas supply pipe connected to the set at a primary connection node, the dimensioning of the set respecting the following relationship:

$$\Sigma\omega_i/\Sigma\phi_i \geq 1 \text{ preferably} \geq 1.5;$$

where $\Sigma\omega_i$ represents the sum of the internal cross sections of the gas supply pipes which feed the set and $\Sigma\phi_i$ represents the sum of the cross sections of the gas injection orifices of the set of ducts.

12 Claims, 2 Drawing Sheets

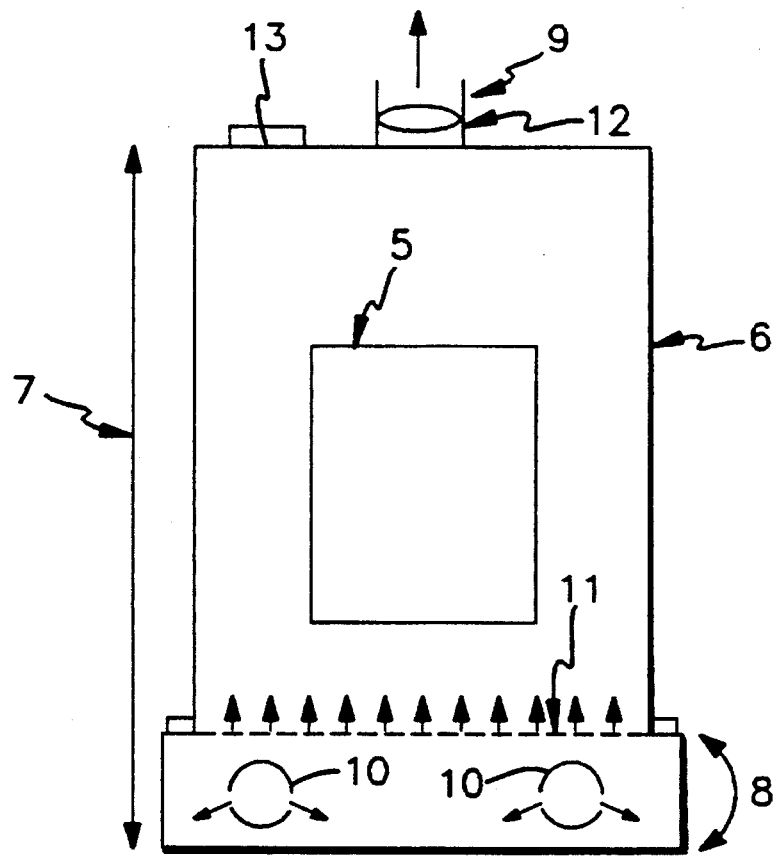
FIG. 2
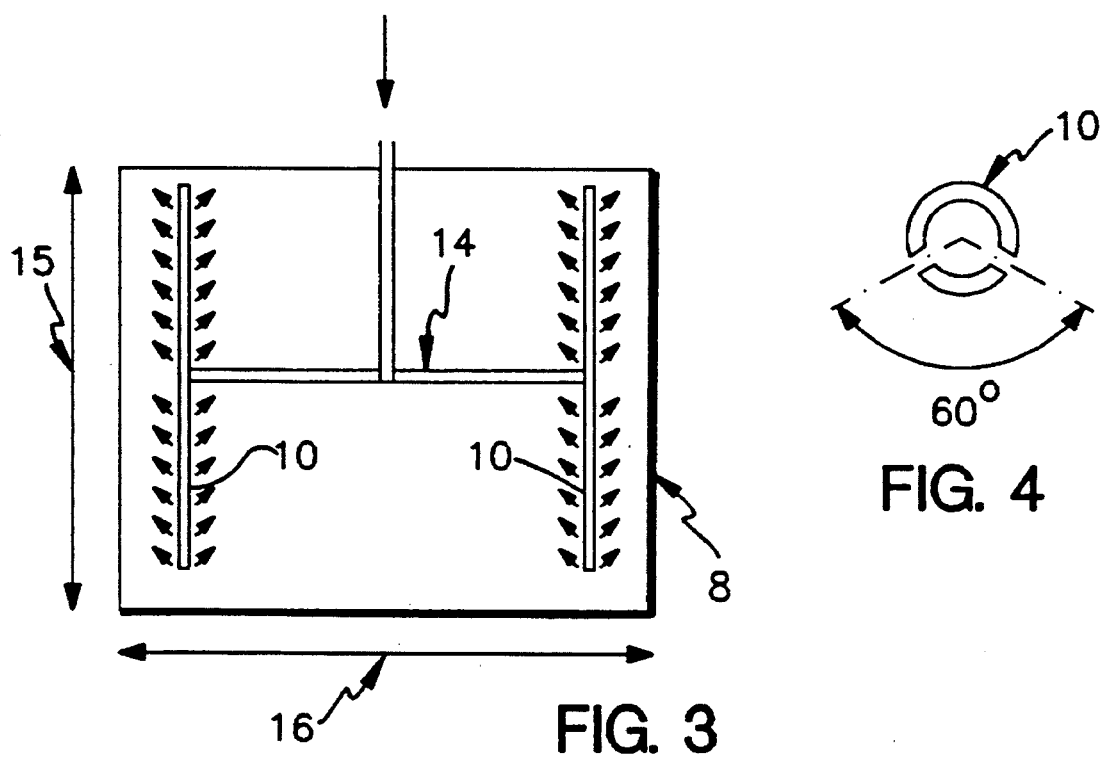
FIG. 3
FIG. 4

5,563,338

1

METHOD AND DEVICE FOR MEASURING WETTABILITY UNDER CONTROLLED ATMOSPHERE

FIELD OF THE INVENTION

The invention relates to apparatuses for measuring solderability or wettability, commonly called "meniscodynamographs" or "meniscographs", or else "wetting balances".

It concerns in particular the steps of evaluating the solderability or wettability of metallic surfaces which are currently carried out in the industry of electronics soldering, either in the case of reflow soldering or in the case of wave soldering.

BACKGROUND OF THE INVENTION

Wave soldering machines are traditionally used for soldering components onto an electronic circuit (either in the case of components inserted into the circuit or components surface-mounted on this circuit), and also for tinning terminations of electronic components or else for soldering contact strips onto electronics supports such as hybrid circuits.

The design of these machines is thus such that, after they have been fluxed in an upstream zone of the machine (principally so as to deoxidize the metallic surfaces in order to facilitate their subsequent wetting by the soldering material), the components to be soldered or to be tinned are brought into contact with one or more waves of liquid soldering material obtained by pumping the soldering material bath contained in a vat through a nozzle.

Application of the chemical flux at the entry of the machine generally gives rise to the requirement for the user to carry out, at the exit of the machine, after soldering or tinning, an operation of cleaning the products, often with the aid of chlorinated solvents, making it possible to remove the flux residues which remain on the circuit or the component.

Although these machines are traditionally open to the ambient air atmosphere, growing use of an inert atmosphere in these wave soldering machines is in practice observed, principally with the aim of avoiding the formation of oxide layers on the surface of the soldering material bath because of its exposure to air, but also in an international environmental protection context, in combination with the use of low-activity flux leaving a very low amount of residue on the circuits, which makes it possible essentially to eliminate the subsequent operation of cleaning these circuits, and therefore the use of toxic solvents.

For its part, reflow soldering relies on a different principle: it consists in depositing a soldering paste on predetermined regions located on the surface of the circuit, in bringing the components and the soldering paste into contact, then in heating the soldering paste so as locally to produce soldered joints. In the case of reflow soldering, the flux is included in the composition of the soldering paste, which furthermore comprises, in particular, a powder of a metallic alloy (most often a tin-lead alloy).

Here again, increasing use of controlled inert atmosphere is observed, both with a desire to improve the quality of the solder joint obtained and also here again to allow the use of soldering pastes containing low-residue fluxes for which it is possible to avoid the final operation of cleaning the circuits.

In this context, the meniscograph is often a key element of the workshop or assembly site in electronics. It is used in particular for evaluating the solderability of the components

2

(qualification test of the components), the wettability of the substrates used for fabricating the circuits, both in the case of substrates of the printed circuit type or hybrid circuits (qualification of the substrates), the wetting time, the efficiency of the fluxes, the efficiency of the soldering creams, etc.

Its principle, which is well known to the person skilled in the art, is that of determining the wetting angle of a solder on a sample (both in the case of a sample of the component type or of the substrate type), by measuring the wetting force exerted by the solder on the surface of the sample during immersion of this sample in a liquid solder bath. A classical relationship connects, in particular, the resultant force (between the wetting force proper and the buoyancy), the wetting angle, the density of the alloy tested, the liquid/ vapour surface tension of the system, and the volume of the sample immersed in the molten alloy.

It is thus classically considered that, for a wetting angle $\theta$ greater than or equal to zero and less than or equal to 30°, the wettability is qualified as being very good, for $\theta$ strictly greater than 30° and less than or equal to 40°, the wettability is qualified as being good, for $\theta$ greater than 40° and less than or equal to 55°, the wettability is acceptable, for an angle $\theta$ strictly greater than 55° and less than or equal to 70°, the wettability is termed low and, finally, for an angle $\theta$ strictly greater than 70°, the wettability is qualified as being poor.

As indicated hereinabove, soldering processes (both in the case, for example, of reflow soldering and wave soldering), have to date been most commonly carried out under ambient air atmosphere. Commercially available meniscographs were therefore perfectly adapted to this situation, having a structure which is open to the surrounding atmosphere.

In the new context of increasing use of controlled inert atmospheres during the soldering processes, the users of these industries are currently showing increasing interest in being able to obtain meniscographs which can operate under protective atmosphere, containing residual concentrations of oxygen which are as low as a few tens of ppm, or even a few ppm of oxygen.

The aim is thus to be able to reproduce the atmosphere conditions produced on a day to day basis in their soldering furnace or machine, including the most severe and restricting conditions of residual oxygen concentrations.

Thus, the requirements most commonly expressed are as follows:

capability of carrying out comparative evaluation tests of the solderability (the two expressions solderability or wettability are both often used equivalently) of the surfaces between a nitrogen atmosphere comprising a determined residual oxygen concentration and a traditional air atmosphere;

qualification of the components and substrates received by the user, under the atmosphere conditions in which they are subsequently treated in the soldering process used.

Fulfilling such desires of users therefore requires controlled (generally inert) atmospheres to be set up in such meniscographs, under conditions making it possible to obtain perfectly controlled residual oxygen concentrations, including very low concentrations.

In this context, it was apparent to the applicants that the solution to be applied to inertness problems posed by users was not only the production of optimized inertness (rapid inertness time, very low residual oxygen concentrations, economically acceptable gas consumption), but also that the atmosphere set up (therefore the corresponding gas injection) does not constitute interference with the measurement, that is to say the high-precision tool constituted by a wetting balance or meniscograph.

Once defined, these two conditions of efficient and rapid inertness and non-interference with the measurement appear relatively incompatible.

In a more general context, the Applicant Company recently proposed, in the French Patent Application filed under No. FR-A-93.15503, a gas injection device for forming a controlled atmosphere in a confined space, which was particularly suitable for setting up a controlled atmosphere in one or more zones of a wave soldering machine, or else in all or part of a continuous furnace used for applications such as soldering or else annealing, tampering, sintering or any other heat treatment.

OBJECTS OF THE INVENTION

The object of the present invention is to provide a novel device for measuring wettability, the configuration of which makes it possible to perform the measurement both in classical conditions of operating under air and in controlled (in particular inert) atmosphere conditions, for which:

an atmosphere substantially depleted in oxygen (residual oxygen concentration which may range from a few ppm to a few tens of thousands of ppm depending on the application of the user) may, if necessary, be reached in a rapid time (not exceeding a few minutes), and with an economically acceptable gas flow rate;

setting up of the controlled atmosphere is produced without interfering with the balance, and therefore without interfering with the measurement.

SUMMARY OF THE INVENTION

To this end, the device making it possible to carry out wettability measurements under a controlled atmosphere according to the invention comprises an apparatus for measuring the wettability of at least one surface portion of a sample by a liquid metallic solder, which apparatus is of the type making it possible to measure the wetting force exerted by the solder on the surface during immersion of all or part of the sample in a bath of said liquid solder, and wherein the apparatus is at least partially included in an enclosure, making it possible to isolate at least the solder bath from the surrounding atmosphere, the enclosure including at its upper part or at its lower part a gas injector which comprises at least one set of ducts mounted in series and/or in parallel, at least one duct portion of which includes gas injection orifices, said set being fed by at least one gas supply pipe, each pipe being connected to the set at a primary connection node, the dimensioning of the set respecting the following relationship:

$$\Sigma\omega_i/\Sigma\phi_i \geq 1 \text{ preferably} \geq 1.5;$$

where $\Sigma\omega_i$ represents the sum of the internal cross sections of the gas supply pipes which feed the set and $\Sigma\phi_i$ represents the sum of the cross sections of the gas injection orifices of the set of ducts.

According to one of the embodiments of the invention, the enclosure includes at its upper part or at its lower part a chamber which is separated from the rest of the enclosure by a diffuser structure and inside which said gas injector is arranged.

The diffuser may then, for example, consist of a perforated sheet. The cavity percentage of the perforated sheet will then advantageously be less than 40%, and preferably less than 20%.

According to another embodiment of the invention, the diffuser consists of a plate made of a porous material.

In order to produce the perforated sheet, use will advantageously be made of a material which resists the temperature classically produced in the environment of a meniscograph such as, for example, stainless steel or else a plastic. As regards the diffuser made of porous material, ceramics may, for example, be envisaged. The materials used will need, in particular, to suit the temperature conditions and also the desired residual oxygen levels, so as not to introduce additional contamination.

The injected gas may be both a neutral gas (such as nitrogen, argon or else helium), in the case of setting up an inert protective atmosphere, and a more active gas such as, for example, hydrogen or inert gas/hydrogen mixtures, or else inert gas/silane mixtures when it is desired to test atmospheres which are desired to play a more active role such as, for example, stripping surfaces.

As regards the inert part of the atmosphere set up, use may be made of a gas obtained cryogenically and also, depending on the desired characteristics (for example the oxygen content), a gas source obtained by air separation by permeation or adsorption.

According to the invention, the term "controlled atmosphere" is used to mean an atmosphere, the composition of which is simply predetermined, optionally measured (either continuously, sequentially or on starting up the device) or regulated (that is to say an atmosphere, the composition of which is kept at the predetermined desired composition by supplying fresh gas).

Thus, by way of illustration, considering the example of a case in which it is desired to maintain an inert atmosphere with controlled oxygen content (for example close to 100 ppm of residual oxygen) inside the device, one of the following operations may be adopted according to the invention:

calibrating the injected mixture so that its composition corresponds to a residual oxygen content of approximately 100 ppm (either in the case, for example, of nitrogen from permeation or adsorption, or else a previously calculated and produced mixture of cryogenic nitrogen/oxygen);

injecting such a mixture and checking by at least one measurement (either a single measurement, for example an initial measurement, or regular measurement) of the atmosphere inside the device as to the residual oxygen concentration; or else injecting such a mixture and regulating the atmosphere inside the device by regular measurement of the residual oxygen concentration and action on the fresh gas supply when a drift in the measured concentration from a selected set-point is observed.

As will be clearly understood by the person skilled in the art, the device according to the invention makes it possible to perform measurements under a controlled atmosphere, and also under classical air atmosphere in order to make comparative measurements.

According to one of the aspects of the invention, at least one of the gas supply pipes of the injector itself includes gas injection orifices.

The dimensioning of the set then follows the following relationship:

$$\Sigma\omega_i/(\Sigma\phi_i+\Sigma\alpha_i) \geq 1, \text{ preferably} \geq 1.5,$$

where $\Sigma\omega_i$ represents the sum of the internal cross sections of said gas supply pipes which feed the set, $\Sigma\phi_i$ represents the sum of the cross sections of the gas injection orifices of the set of ducts and $\Sigma\alpha_i$ represents the sum of the cross sections of the injection orifices of the pipes(s): in question which includes (include) gas injection orifices.

According to another aspect of the invention, the pipes for feeding gas to the set all come from an upstream node, itself fed with gas by a feed conduit of internal cross section $\Omega$, the dimensioning of this upstream node being such that:

$$\Omega/\Sigma\omega_i \geq 1, \text{ preferably} \geq 1.5,$$

where $\Sigma\omega_i$ represents the sum of the internal cross sections of the supply pipes.

In such a configuration having an upstream node, if one (or more) of the gas supply pipes itself (themselves) includes (include) gas injection orifices, the dimensioning of the set then follows the following relationship:

$$\Omega/(\Sigma\phi_i + \Sigma\alpha_i) \geq 1 \text{ preferably} \geq 1.5,$$

where $\Sigma\phi_i$ represents the sum of the cross sections of the gas injection orifices of the set of ducts, $\Sigma\alpha_i$ represents the sum of the cross sections of the injection orifices of the gas pipe(s) which includes (include) gas injection orifices and $\Omega$ represents the internal cross section of the feed conduit.

For each duct or supply pipe including gas injection orifices, these orifices are preferably directed toward the top of the enclosure when the injector is located in the upper part of the enclosure and toward the bottom of the enclosure when the injector is located in the lower part of the enclosure.

As regards definitions of the intended meanings of "node", "ducts" and "conduits", "gas injection orifices" according to the invention, reference will be made to the abovementioned document FR-A-93.15503. It will here simply be mentioned that, according to the invention, the terms "duct" and "conduit" mean any type of gas transport or feed duct, whether it be straight, as is the classical case, or curved, of, for example, circular or else square or rectangular cross section, made of materials which vary widely depending on the gas in question (chemical compatibility), for example made of stainless steel, copper, PVC, etc.

The "gas injection orifices" optionally present on some of these ducts or supply pipes should then be understood as being holes allowing the gas to escape from said duct or pipe, generally transversely to its direction of flow through the duct or pipe (depending on the shape of the holes).

According to the invention, the term "node" is intended to mean either a simple connection point or a suitable device (of the buffer chamber type) defining a volume in which the gas conveyed by the pipe emerges, and from which it departs to the duct subassembly with which it communicates.

In the case in which the injector is reduced to a simple duct including orifices, which is fed with gas at one of its ends, the relationship $\Sigma\omega_i/\Sigma\phi_i \geq 1$ will take into account a single $\omega_i$ which represents the internal cross section of the duct itself and $\Sigma\phi_i$ which represents the sum of the cross sections of the injection orifices of the duct, the "primary node" according to the invention then being in this case an "imaginary" intermediate connection point between the end of the duct and the part of the duct including orifices.

According to one of the embodiments of the invention, when the assembly contains one or more duct portions of square or rectangular cross section including gas injection orifices and/or one or more supply pipes including gas injection orifices, these portions or supply pipes consist of a lower non-perforated U-shaped part on which a perforated sheet of inverted U-shape is mounted.

According to one of the embodiments of the invention, the enclosure is equipped with at least one channel for removing the injected gas.

The invention also relates to a method for measuring under controlled atmosphere the wettability of a surface by a liquid metallic solder, wherein use is made of a device such as that previously described and wherein a gas is injected through said injector, the speed of the gas at the outlet of the gas injection orifices of the set(s) of ducts then preferably being greater than 0.5 meters/second, and more preferably greater than 1 meter/second.

According to one of the aspects of the invention, the Reynolds number of the gas flow at the outlet of the set and/or at the outlet of the diffuser is less than 2,000, so as to achieve a flow regime which is as close as possible to the laminar regime (the Reynolds number being calculated by the ratio $V \times D/\nu$, where V represents the mean velocity of the gas at the outlet of an injection orifice, D represents the internal diameter of this orifice and $\nu$ represents the kinematic viscosity of the gas in question).

BRIEF DESCRIPTION OF THE INVENTION

Other features and advantages of the present invention will emerge from the following description of embodiments given by way of illustration but without implying any limitation, made with reference to the attached drawings, in which:

FIG. 1 of the present application gives a schematic perspective representation of a chamber according to the invention including an injector;

FIG. 2 of the present application schematically illustrates an example of a device suitable for implementing the invention;

FIG. 3 gives a schematic representation in plan view of the chamber of the device in FIG. 2 and of the injector which it includes; and FIG. 4 gives the detail in cross section of the structure of the two ducts in FIG. 3.

DETAILED DESCRIPTION OF THE INVENTION

Figure 1:
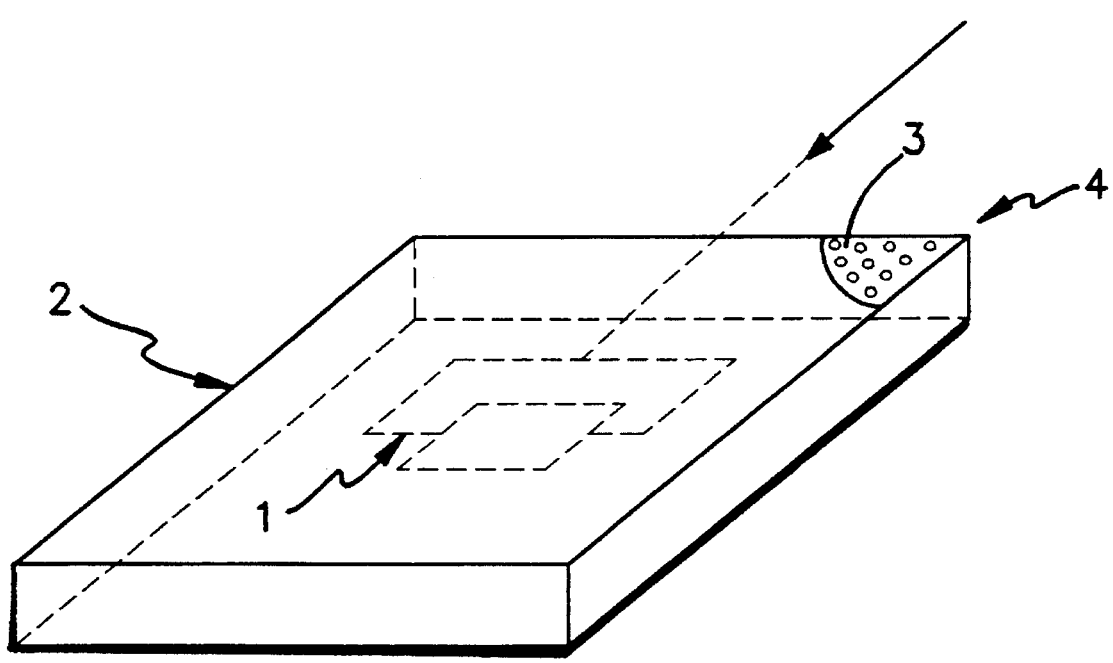

FIG. 1 of the present application schematizes a chamber suitable for implementing the invention, including a set of ducts 1 (simply schematized here in the form of a broken line), included in a hood 2, the upper part 3 of which consists of a diffuser structure partially schematized at the corner 4 of the hood.

FIG. 2 illustrates an example of a device suitable for implementing the invention. This figure shows the presence of a meniscograph schematized at 5, included in an enclosure 6 including in its lower part a chamber 8 in which an injector which will be detailed hereinbelow in the context of FIG. 3 is arranged, this injector including two ducts 10. The chamber 8 includes in its upper part a diffuser structure 11 separating it from the rest of the enclosure and, in particular, from the meniscograph. The arrow 7 represents an order of magnitude of the height of the enclosure, here, for the example represented, of the order of 1.2 meters.

The apparatus (meniscograph) 5 rests, for example, on a system of transverse bars (not represented in FIG. 2) arranged through the enclosure at a greater or lesser distance above the diffuser.

The presence in the upper part of the enclosure of a gas removal channel 9, fitted with a flap valve 12 making it possible to maintain the enclosure under pressure, and the presence at 13 of a safety valve will be noted.

FIG. 3 allows better visualization in plan view of the structure of the chamber 8 and of the injector located therein (the structure of the diffuser is not represented for reasons of clarity). The injector 14 includes two ducts 10 equipped with injection orifices.

The symbolized arrows 15 and 16 give an order of magnitude of the dimensions of the chamber 8, for the case represented here, of the order of 80 cm in the case of one of the dimensions and 60 cm in the case of the second dimension.

Each of the two ducts 10 includes, for example, two rows of fifteen orifices having a diameter of 4 mm, thus giving rise to the presence of 60 holes overall. For the example illustrated, and for each duct 10, which is here made of plastic, the two rows of holes are directed toward the bottom of the enclosure (FIG. 4), that is to say toward the face of the chamber opposite the diffuser structure 11, with the presence of a 60° angle between the two rows of orifices.

The duct 10 given as an example in the context of FIGS. 2, 3 and 4 has an external diameter of 32 mm, the thickness of the material being 2.4 mm.

A device such as that described in the context of FIGS. 2, 3 and 4 was tested under the following operating conditions:

the solderability measurement apparatus 5 is a meniscograph of brand "METRONELEC", reference ST40;

the injector 14 respects the dimensioning rules according to the invention;

the diffuser 11 is a stainless steel mesh, the aperture percentage of which is 23%;

the enclosure was flushed through the diffuser 11 by injecting a flow rate of 20 m$^3$/hour of nitrogen into the injector 14. The nitrogen used is nitrogen of the cryogenic type containing less than 5 ppm of residual oxygen.

The tests carried out had the purpose of demonstrating that the device according to the invention:

does not introduce overheating of the atmosphere around the soldering bath;

while allowing rapid conditioning of the atmosphere;

without interfering with the measurement obtained by the wetting force sensor.

First test: removal of heat

With the force measurement apparatus 5 turned on (the soldering material bath therefore being hot) and placed inside the enclosure 6, the enclosure was flushed with the aforementioned gas flow rate.

A thermocouple present in the vicinity of the soldering material bath made it possible to check during all the operations that the act of working in an enclosed system did not cause overheating of the measurement atmosphere.

Second test: conditioning of the atmosphere

With the enclosure 6 initially containing an air atmosphere, 20 m$^3$/hour of nitrogen are injected. After flushing for 15 minutes, an analysis of the atmosphere present inside the enclosure made it possible to measure a residual oxygen level of less than 20 ppm. The device according to the invention therefore allowed rapid conditioning of the atmosphere, in view of the relatively large volume of the enclosure around the apparatus 5.

Third test: lack of interference with the measurement

In order to check this lack of interference with the measurement due to setting up of a controlled atmosphere around the measurement apparatus, comparative tests were carried out with the following atmospheres:

ambient air (open system);

reconstituted air (80% nitrogen, 20% oxygen): injected in a closed system with an overall flow rate of the order of 20 m$^3$/hour;

nitrogen alone (cryogenic source): closed system with overall flow rate of the order of 20 m$^3$/hour.

For each measurement atmosphere, the efficiency of commercially available wave soldering fluxes was evaluated, while respecting the operating procedure described in French Standard NF C 90-551.

Fluxes tested

Flux A: non-volatile residues=25% (high residue level);

Flux B: non-volatile residues=2.5% (low residue level).

These commercially available fluxes A and B are widely used in the industry and are therefore representative of commonly employed industrial conditions.

Calibrated samples, the wettability of which was tested

Grade I and grade II copper samples according to Standard NF C 90-551.

Solder used

A liquid bath of approximately 1.4 kg of tin/lead solder (Sn60-Pb40).

For each set of parameters tested (one atmosphere, one flux, one grade of copper), approximately ten tests were carried out, the result of each test being the maximum wetting force recorded throughout immersion of the sample.

The results given hereinbelow in each case represent the maximum force "averaged" over the ten tests and the corresponding standard deviation,

Flux A/copper grade I reconstituted air: Fmax=7.53 mN, standard deviation=0.05 air: Fmax=7.58 mN, standard deviation=0.05 nitrogen: Fmax=8.18 mN, standard deviation=0.1

Flux A/copper grade II reconstituted air: Fmax=7.52 mN, standard deviation=0.065 air: Fmax=7.57 mN, standard deviation=0.08 nitrogen: Fmax=8.34 mN, standard deviation=0.11

Flux B/copper grade I reconstituted air: Fmax=7.3 mN, standard deviation=0.33 air: Fmax=7.51 mN, standard deviation=0.36 nitrogen: Fmax=8.19 mN, standard deviation=0.28

Flux B/copper grade II reconstituted air: Fmax=6.45 mN, standard deviation=0.99 air: Fmax=6.29 mN, standard deviation=1.07 nitrogen: Fmax=7.82 mN, standard deviation=0.42

The result of these comparative tests clearly shows that the results of the tests obtained under ambient air (open system) and under reconstituted air (closed system) are statistically identical, and therefore that setting up a controlled atmosphere in the enclosure did not interfere with the measurement.

The results of the tests obtained under nitrogen made it possible to verify the results published in the literature, according to which the wetting obtained under protective atmosphere (reduced residual oxygen concentration) is systematically improved compared with classical operation under air (Fmax under $N_2$ greater than Fmax under air).

Thus, these tests therefore made it possible to demonstrate that the wettability measurement device according to the invention makes it possible to perform measurements under controlled atmosphere, either under air or, for example, an inert atmosphere, and to do this under rapid and economically acceptable atmosphere conditioning conditions and without interfering with the operation of the measurement apparatus.

Although the present invention has been described with reference to particular embodiments, it is in no way limited thereby but, moreover, may receive modifications and variants which will occur to the person skilled in the art in the context of the claims hereinbelow.

We claim:

1. A device making it possible to carry out wettability measurements under a controlled atmosphere, comprising an apparatus (5) for measuring the wettability of at least one surface portion of a sample by a liquid metallic solder, which apparatus makes it possible to measure the wetting force exerted by the solder on the surface during immersion of at least a part of the sample in a bath of said liquid solder, wherein the apparatus is at least partially included in an enclosure (6), making it possible to isolate at least the solder bath from the surrounding atmosphere, the enclosure including a gas injector (1, 14) which comprises at least one set of ducts (10), at least one duct portion of which includes gas injection orifices, said set being fed by at least one gas supply pipe, said at least one pipe being connected to the set at a primary connection node, the dimensioning of the set respecting the following relationship:

$$\Sigma\omega_i/\Sigma\phi_i \geq 1;$$

where $\Sigma\omega_i$ represents the sum of the internal cross sections of the gas supply pipes which feed the set and $\Sigma\phi_i$ represents the sum of the cross sections of the gas injection orifices of the set of ducts.

2. The device as claimed in claim 1, wherein the enclosure includes a chamber (8) which is separated from the rest of the enclosure by a diffuser structure (11) and inside which said gas injector (1, 14) is arranged.

3. The device as claimed in claim 2, wherein the diffuser (11) consists of a perforated sheet.

4. The device as claimed in claim 3, wherein the cavity percentage of the perforated sheet is less than 40%.

5. The device as claimed in claim 2, wherein the diffuser consists of a plate made of a porous material.

6. The device as claimed in claim 1, wherein the supply pipes for feeding gas to the set all come from an upstream node, itself fed with gas by a feed conduit of internal cross section $\Omega$, the dimensioning of this upstream node being such that:

$$\Omega/\Sigma\omega_i \geq 1,$$

where $\Sigma\omega_i$ represents the sum of the internal cross sections of said supply pipes.

7. The device as claimed in claim 6, wherein said at least one gas supply pipe itself includes gas injection orifices and wherein the dimensioning of the set then follows the following relationship:

$$\Omega/(\Sigma\phi_i+\Sigma\alpha_i) \geq 1,$$

where $\Sigma\phi_i$ represents the sum of the cross sections of the gas injection orifices of the set of ducts, and $\Sigma\alpha_i$ represents the sum of the cross sections of the injection orifices of the pipe and $\Omega$ represents the internal cross section of said feed conduit.

8. The device as claimed in claim 1, wherein said at least one gas supply pipe itself includes gas injection orifices and wherein the dimensioning of the set then follows the following relationship:

$$\Sigma\omega_i/(\Sigma\phi_i+\Sigma\alpha_i) \geq 1,$$

where $\Sigma\omega_i$ represents the total internal cross section of said at least one gas supply pipe which feeds the set, $\Sigma\phi_i$ represents the sum of the cross sections of the gas injection orifices of the set of ducts and $\Sigma\alpha_i$ represents the sum of the cross sections of the injection orifices of the pipe.

9. The device as claimed in claim 1 wherein, for each duct or pipe including gas injection orifices, these orifices are directed toward a top of the enclosure when the injector is located in an upper part of the enclosure and toward a bottom of the enclosure when the injector is located in a lower part of the enclosure.

10. The device as claimed in claim 1, wherein the enclosure is equipped with at least one channel (9) for removing the gas.

11. A method for measuring under controlled atmosphere the wettability of a surface by a liquid metallic solder, wherein use is made of a device as claimed in claim 1, and wherein a gas is injected through said injector, the speed of the gas at the outlet of the gas injection orifices of the ducts being greater than 0.5 meters/second.

12. The method as claimed in claim 11, wherein the Reynolds number of the gas flow at one of the outlet of the set and the outlet of the diffuser is less than 2,000.

* * * * *